United States Patent [19]

Karol

[11] Patent Number: 5,026,865

[45] Date of Patent: Jun. 25, 1991

[54] SUBSTITUTED 2,5-DIMERCAPTO-1,3,4-THIADIAZOLES AND LUBRICATING COMPOSITIONS CONTAINING SAME

[75] Inventor: Thomas J. Karol, Norwalk, Conn.

[73] Assignee: R. T. Vanderbilt Company, Inc., Norwalk, Conn.

[21] Appl. No.: 56,917

[22] Filed: Jun. 3, 1987

Related U.S. Application Data

[63] Continuation-in-part of Ser. No. 759,211, Jul. 26, 1985, abandoned.

[51] Int. Cl.$^5$ ................ C07C 285/125; C10M 135/36
[52] U.S. Cl. ..................................... 548/142; 252/475
[58] Field of Search ..................... 548/142; 252/47.5

[56] References Cited

U.S. PATENT DOCUMENTS

| | | | |
|---|---|---|---|
| 2,850,453 | 9/1958 | Fields | 252/32.7 |
| 4,306,988 | 12/1981 | Rothgery | 252/150 |
| 4,410,703 | 10/1983 | Okorodudu | 548/142 |
| 4,432,847 | 2/1984 | Fields | 204/158 R |

FOREIGN PATENT DOCUMENTS 0166696 1/1986 European Pat. Off. .

OTHER PUBLICATIONS

*Chemical Abstracts*, vol. 45, Abstract 4239d, 1951. E. Ziegler et al., Monatsh. 81,848, 1950.

*Primary Examiner*—Robert Gerstl
*Attorney, Agent, or Firm*—Rasma B. Balodis

[57] ABSTRACT

Disclosed are novel reaction products of 2,5-dimercapto-1,3,4-thiadiazole and epoxy compounds. These compounds are shown to be effective antiwear agents and antioxidants in lubricating compositions.

4 Claims, No Drawings

SUBSTITUTED 2,5-DIMERCAPTO-1,3,4-THIADIAZOLES AND LUBRICATING COMPOSITIONS CONTAINING SAME

This application is a continuation-in-part of patent application Ser. No. 759,211 filed July 26, 1985, abandoned.

BACKGROUND OF THE INVENTION

The present invention concerns novel derivatives of thiadiazole compounds and their use as functional additives for oil-based and water-based lubricating compositions. More particularly the new thiadiazoles are derived from 2,5-dimercapto-1,3,4-thiadiazole and epoxy compounds.

Additives known as antiwear agents are employed to increase the load-carrying capacity of lubricants. The antiwear agents promote the formation of a surface film and thereby prevent wear of the contacting surfaces.

During the course of use, lubricants are susceptible to deterioration due to oxidation. The oxidative process leads to the loss of lubricating properties and inadequate protection of the device to be lubricated. Antioxidants are added to inhibit the oxidative process. Thus, it is desirable that antiwear agents possess antioxidant properties.

Prior art has disclosed certain thiadiazole type compounds and their use as lubricating additives. However, due to stricter environmental controls, there is a need to develop new and effective ashless-type additives, preferably possessing multifunctional properties.

No art is known that teaches or suggests the present compounds or their use as multifunctional lubricating additives.

SUMMARY OF THE INVENTION

In accordance with the invention, there are provided novel reaction products of 2,5-dimercapto-1,3,4-thiadiazole and a substituted epoxy compound. The reaction products may be characterized by the structural formula

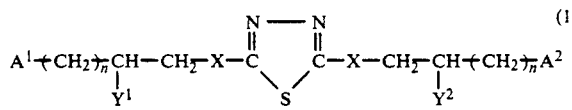 (1)

wherein
X represents —S—,

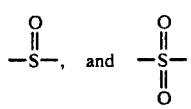

groups;
Y$^1$ and Y$^2$ represent —OH,

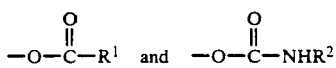

groups;
A$^1$ and A$^2$ represent hydrogen, hydroxy, hydrocarbyl, hydrocarbyloxy and hydrocarbylthio radicals wherein the hydrocarbyl is selected from the group consisting of alkyl, alkenyl, alkynyl, alkaryl, aryl, aralkyl, and cycloalkyl and may further contain an inert substituent group;

R$^1$ and R$^2$ represent an alkyl, alkenyl, alkynyl, aryl, aralkyl, alkaryl and cycloalkyl group; and n is 1, provided that Y$^1$ and Y$^2$ are not —OH when X is —S— or

 (2)

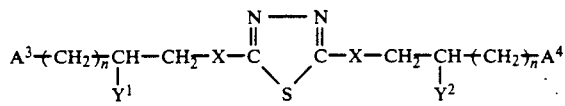

wherein
X represents —S—,

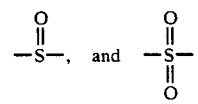

groups;
Y$^1$ and Y$^2$ represent —OH,

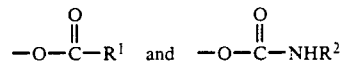

groups;
A$^3$ and A$^4$ represent hydrocarbyl radicals wherein the hydrocarbyl is selected from the group consisting of alkaryl, aryl, and cycloalkyl and may further contain an inert substituent group;

R$^1$ and R$^2$ represent an alkyl, alkenyl, alkynyl, aryl, aralkyl, alkaryl and cycloalkyl group; and n is 0 provided that Y$^1$ and Y$^2$ are not —OH when X is —S— or

Another aspect of the invention concerns oil-based and water-based compositions containing the novel reaction products and similar known compounds in an amount sufficient to impart antiwear and antioxidant properties and characterized by the structural formulae

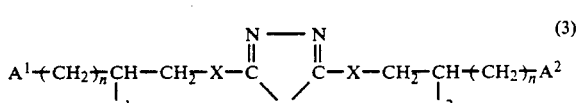 (3)

wherein X represents —S—,

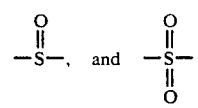

groups;
Y$^1$ and Y$^2$ represent —OH,

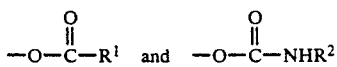

groups;

$A^1$ and $A^2$ represent hydrogen, hydroxy, hydrocarbyl, hydrocarbyloxy and hydrocarbylthio radicals wherein the hydrocarbyl is selected from the group consisting of alkyl, alkenyl, alkynyl, alkaryl, aryl, aralkyl, and cycloalkyl and may further contain an inert substituent group;

$R^1$ and $R^2$ represent an alkyl, alkenyl, alkynyl, aryl, aralkyl, alkaryl and cycloalkyl group; and n is 1 and

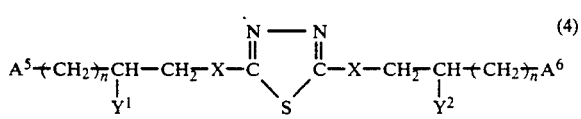

(4)

wherein X represents —S—,

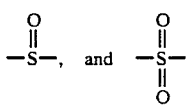

groups;

$Y^1$ and $Y^2$ represent —OH,

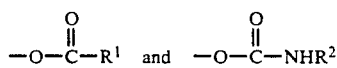

groups;

$A^5$ and $A^6$ represent hydrogen and hydrocarbyl radicals wherein the hydrocarbyl is selected from the group consisting of alkaryl, aryl, aralkyl, and cycloalkyl and may further contain an inert substituent group;

$R^1$ and $R^2$ represent an alkyl, alkenyl, alkynyl, aryl, aralkyl, alkaryl and cycloalkyl group; and n is 0 provided that $Y^1$ and $Y^2$ are —OH or

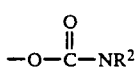

groups when X is —S—.

DESCRIPTION OF SPECIFIC EMBODIMENTS

The reaction products of the invention may be prepared by reacting 2,5-dimercapto-1,3,4-thiadiazole with two molar equivalents of an epoxy compound to form the corresponding alcohol derivative. Further novel reaction products may be formed from the alcohol derivative by reacting with an alcohol reactive functional group. Thus, esters may be formed by esterification with an organic acid or an equivalent thereof as for example organic acid halide or organic acid anhydride. Other products may be formed by reacting the alcohol derivative with an isocyanate compound. All of the hereinabove described products may be oxidized by known methods to form the corresponding sulfonyl and sulfinyl derivatives.

The general reaction scheme is illustrated by the following equation wherein 2,5-dimercapto-1,3,4-thiadiazole is reacted with 2 moles of propylene oxide to form the corresponding alcohol and then esterified with acetic anhydride.

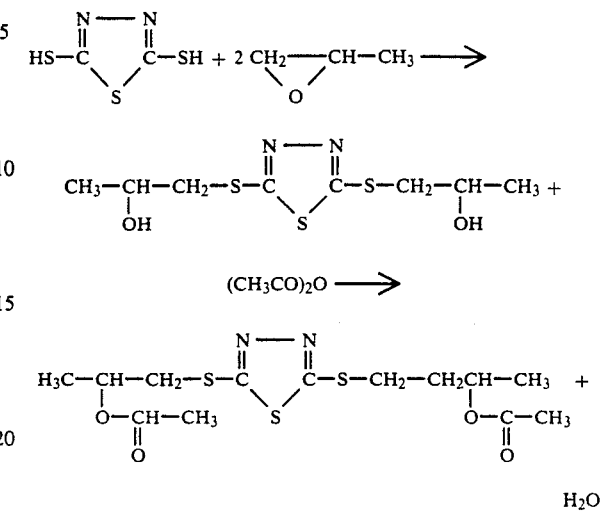

Preferably, the reaction with epoxides may be conducted in the presence of an inert solvent such as alcohols, toluene and benzene and a reaction promoter as for example tertiary amines. The reaction temperature will depend upon the specific reactants and solvent media employed. Typically reaction temperatures range from about 80° C. to 140° C.

The reaction illustrated by the equation is the preferred method. Other methods of synthesis may be used.

The hydrocarbyl groups ($A^1$ and $A^2$) and ($R^1$ and $R^2$) in formula (1) represent an alkyl group having from 1 to 100 carbon atoms and a straight or branched chain including alkyls substituted by an aryl, an alkenyl group, an alkynyl group, a cycloalkyl group including cycloalkyl substituted with an alkyl, an aryl group having 6 to 14 carbon atoms including aryls substituted by an alkyl. These include, among others, methyl, ethyl, n-propyl, iso-propyl, n-butyl, iso-butyl, sec-butyl, pentyl, octyl, dodecyl, octadecyl, polymeric alkyl, benzyl, beta-phenylethyl, vinyl, allyl, 1-butenyl, ethynyl, propynyl, butynyl, cyclohexyl, cycloheptyl, cyclooctyl, 2-methylcycloheptyl, 3-butylcyclohexyl, phenyl, naphthyl. The hydrocarbyl groups may further bear a nonreactive substituent such as, among others, alkyl, aryl, cycloalkyl, ether, amide, urea, halo and nitro groups. These include, among others, 3-chloropropyl, 2-ethoxyethyl, o-chlorophenyl, p-chlorobenzyl, 3-chloro-5-methylphenyl, dodecyloxymethyl, and butyloxymethyl.

The hydrocarbyl groups ($A^1$) and ($A^2$) may be the same or different. Similarly the hydrocarbyl groups ($R^1$) and ($R^2$) may be the same or different.

The thiadiazole derivatives of the invention are useful as lubricating additives. The compounds possess multifunctional properties with respect to antiwear and oxidation inhibition. Although no particular theory is hereby relied on, the mercaptothiadiazoles are expected to be oxidized in performing the antioxidant role. These oxidized analogs still retain antiwear properties. Thus, the compounds are truly bifunctional.

The thiadiazoles may be incorporated into lubricating compositions. Preferred are thiadiazole reaction products of formula (1) wherein the radicals contain from 1 to 75 carbon atoms and preferably from 1 to 50 carbon atoms.

The lubricating compositions contemplated herein include lubricating oils and lubricating greases containing a major amount of base oil. The base oil may be selected from oils derived from petroleum hydrocarbon and synthetic sources. The hydrocarbon base oil may be selected from naphthenic, aromatic, and paraffinic mineral oils. The synthetic oils may be selected from, among others, alkylene polymers, polysiloxanes, carboxylic acid esters and polyglycol ethers.

Another lubricating composition useful herein includes water-based systems. Typically the aqueous systems comprise at least 40 percent of water and zero to less than 15 percent of base oil. Oil-soluble additives are incorporated in the system with the aid of solubilizer/stabilizer systems. The water based systems are useful not only as lubricants, but also as functional fluids such as cutting oils, hydraulic fluids, and transmission fluids.

The amount of the thiadiazole additive required to be effective for imparting antiwear and antioxidant characteristics in lubricating compositions may range from about 0.01 to 10 percent of the lubricating composition. The preferred range is about 0.1 to 5.0 percent of the additive of the total lubricating composition.

The lubricating compositions may contain the necessary ingredients to prepare the composition as for example dispersing agents, emulsifiers and viscosity improvers. Greases may be prepared by addition of thickeners as for example salts and complexes of fatty acids, polyurea compounds, clays and quaternary ammonium bentonite. Depending on the intended use of the lubricant, other functional additives may be added to enhance a particular property of the lubricant. The lubricating compositions may further contain known antioxidants, extreme pressure agents, metal passivators, rust inhibitors and other antiwear agents.

The following examples are given for the purpose of further illustrating the invention. All percentages and parts are based on weight unless otherwise indicated.

EXAMPLE 1

2,5-Bis(3-dodecyloxy-2-hydroxypropylthio-1,3,4-thiadiazole 2,5-Dimercapto-1,3,4-thiadiazole(79.9 grams, 0.53 moles) was charged into a reaction flask followed by isopropanol solvent, 200 ml. The epoxide, dodecyl glycidyl ether (272.4 grams, 1.06 moles) was added slowly to the reactor with stirring. The reaction mixture was heated at about 80° C. for 0.5 hours. At this time the solvent was stripped by using a rotary evaporator at approximately 20 mm Hg and 100° C. The product was a low melting solid characterized by the infrared absorption bands at 3400, 2900, 1460, 1380, 1120, and 1050 cm$^{-1}$.

EXAMPLE 2

2,5-Bis(3-octyloxy-2-hydroxypropylthio-1,3,4-thiadiazole

The product was prepared substantially in accordance with the procedure described in Example 1 except that the epoxide used was octyl glycidyl ether. The product was characterized by the infrared absorption bands at 3400, 2900, 1460, 1380, 1260, 1120, and 1050 cm$^{-1}$.

EXAMPLE 3

2,5-Bis(3-butyloxy-2-acetoxypropylthio-1,3,4-thiadiazole 2,5-Dimercapto-1,3,4-thiadiazole(50.2 grams) and acetic anhydride(85 grams) were charged into a reaction flask. The epoxide, butyl glycidyl ether, was slowly added with warming to initiate the reaction. The reaction mixture was stirred at approximately 80° C. for 0.5 hours. Triethylamine(0.5 ml) was added and the mixture was heated to 130° C. for 0.5 hours. At this time the solvent was stripped by using a rotary evaporator at approximately 20 mm Hg and 100° C. The product was characterized by the infrared absorption bands at 3450, 2900, 1750, 1695, 1460, 1370, 1230, 1120, 1035, and 735 cm$^{-1}$.

EXAMPLE 4

2,5-Bis(2-hydroxyhexadecylthio)-1,3,4-thiadizole 2,5-Dimercapto-1,3,4-thiadiazole(50.03 grams) and 1,2-epoxyhexadecane(163 grams) were charged to the reaction flask with cooling to maintain the temperature below 100° C. The reaction mixture was stirred at 85° to 100° C. for 0.5 hours. The reaction yielded a product which solidified below 85° C. and was characterized by the infrared absorption bands at 3405, 2900, 1465, 1390, 1100, and 720 cm$^{-1}$.

EXAMPLE 5

2,5-Bis(3-dodecylthio-2-hydroxypropylthio)-1,3,4-thiadiazole

In a reaction flask, isopropanol (100 ml),dodecylmercaptan (30.66 grams, 0.151 moles),and sodium hydroxide pellets(6.1 grams, 0.153 moles) were mixed with stirring. In another flask 2,5-dimercapto-1,3,4-thiadiazole (11.3 grams, 0.076 moles) and epichlorohydrin(14 grams, 0.151 moles) were reacted in isopropanol(100 ml) by heating to reflux temperature. The reacted mixture was added to the reaction flask and refluxed for 0.5 hours. The solvent was stripped off to produce a yellow oil product characterized by the infrared absorption bands at 3400, 2900, 1680, 1460, 1380, 1040, and 720 cm$^{-1}$.

EXAMPLE 6

2-(3-Dodecyloxy-2-hydroxypropylthio)-5-(3-butyloxy-2-hydroxypropylthio)-1,3,4-thiadiazole 2,5-Dimercapto-1,3,4-thiadiazole(51.64 grams, 0.34 moles) and isopropanol(150 ml) were added to the reaction flask. Dodecyl glycidyl ether(87.35 grams, 0.34 moles) was slowly added with cooling to maintain the temperature below 25° C. Then sodium hydroxide(0.05 grams) was added followed by butyl glycidyl ether (44.91 grams, 0.34 moles). The reaction mixture was refluxed for 15 minutes and the solvent was stripped off by using a rotary evaporator. The product was characterized by infrared absorption bands at 3200, 2900, 1460, 1385, 1260, 1120, 1050, and 710 cm$^{-1}$.

EXAMPLE 7

2,5-Bis(2-hydroxy ethylthio)-1,3,4-thiadiazole 2,5-Dimercapto-1,3,4-thiadiazole(80.6 grams, 0.54 moles) and ethanol (150 ml) were charged into reaction flask and stirred. The flask was flushed with nitrogen and then ethylene oxide (54 grams, 1.3 moles) was added slowly via a gas inlet directly above the surface of the solution. The reaction mixture was refluxed with stirring for 15 minutes. The solvent was stripped off by using a rotary evaporator at approximately 20 mm Hg and 100° C. The product was a white solid and characterized by infrared absorption bands at 3350, 2900, 1675, 1385, 1285, 1050, 750, and 710 cm$^{-1}$.

EXAMPLE 8

2,5-Bis(2-hydroxypropylthio)-1,3,4-thiadiazole 2,5-Dimercapto-1,3,4-thiadiazole(276.21 grams, 1.84 moles) and isopropanol (400 ml) were charged into a reaction flask. Propylene oxide(222.8 grams, 3.84 moles) was added at a rate sufficient to maintain reflux condition. The mixture was refluxed for 15 minutes. The solvent was stripped off by using a rotary evaporator at approximately 20 mm Hg and 100° C. The product is characterized by infrared absorption bands at 3350, 2900, 1680, 1450, 1380, 1250, 1120, 1040, 930, 740, and 705 cm$^{-1}$.

EXAMPLE 9

2,5-Bis(3-butyloxy-2-hydroxypropylthio)-1,3,4-thiadiazole

The product was prepared substantially in accordance with the procedure described in Example 8 except that the epoxide used was butyl glycidyl ether. The product was a light yellow liquid which was characterized by infrared absorption bands at 3400, 1460, 1385, 1120, 1040, and 740 cm$^{-1}$.

EXAMPLE 10

2,5-Bis(3-phenyloxy-2-hydroxypropylthio)-1,3,4-thiadiazole

Phenyl glycidyl ether (179.4 grams, 1.20 moles) and isopropanol (200 ml) were charged into the reaction vessel. 2,5-Dimercapto-1,3,4-thiadiazole (85 grams, 0.568 moles) was added in increments and with stirring. The reaction mixture was refluxed for 5 minutes. The solvent was stripped off by using a rotary evaporator at about 20 mm Hg and 115° C. The product solidified on cooling and was characterized by the infrared absorption bands at 3400, 3060, 2920, 1600, 1500, 1380, 1240, 1040, 750, and 690 cm$^{-1}$.

EXAMPLE 11

2,5-Bis(2-acetoxyhexadecylthio)-1,3,4-thiadiazole

The product of Example 4 (1.5 grams), acetic anhydride (2 grams), toluene (5 ml), and triethylamine (0.1 grams) were charged into a reaction vessel and refluxed for one hour. The solvent was stripped off by using a rotary evaporator at about 20 mm Hg and 100° C. The product was characterized by infrared absorption bands at 2900, 1750, 1460, 1370, 1230, and 1035 cm$^{-1}$.

EXAMPLE 12

2,5-Bis(2-acetoxypropylthio)-1,3,4-thiadiazole

The product was prepared substantially in accordance with Example 3 except that the epoxide was propylene oxide and the reaction was conducted at reflux temperature for 45 minutes. The product was characterized by the infrared bands at 2950, 1735, 1690, 1450, 1370, 1230, 1125, 1035, and 950 cm$^{-1}$.

EXAMPLE 13

2,5-Bis(3-dodecyloxy-2-hydroxypropylsulfonyl)-1,3,4-thiadiazole

The product of Example 1 (51.10 grams, 0.77 moles) and n-propanol (250 ml) were charged into a reaction vessel. A solution of 70% hydrogen peroxide (19.1 grams, 0.39 moles) was slowly added and the reaction mixture was refluxed for 0.5 hours. The product was extracted with about 150 ml of hexane and washed with five 300 ml portions of water. The extracted layer was dried over magnesium sulfate, filtered, and stripped of the solvent as in Example 1. The product was characterized by infrared absorption bands at 3400, 2900, 1750, 1710, 1465, 1380, 1250, and 1120 cm$^{-1}$.

EXAMPLE 14

2,5-Bis(3-hydroxy-2-hydroxypropylthio)-1,3,4-thiadiazole

The product was prepared according to the procedure described in Example 2 using glycidol as the epoxide. The viscous liquid product was purified by diluting with an equal weight of water and filtering. The product was characterized by the infrared absorption bands at 3350, 1650, 1385, and 1050 cm$^{-1}$.

EXAMPLE 15

2,5-Bis[2-(butylcarbamoyl)butylthio]-1,3,4-thiadiazole 2,5-Dimercapto-1,3,4-thiadiazole (30.92 grams, 0.206 moles) and hexane (30 ml) were charged into the reaction vessel and warmed. 1,2-Epoxybutane (30.2 grams, 0.419 moles) was slowly added with stirring and the mixture was refluxed for 0.5 hours with vigorous stirring. Triethylamine (0.5 ml) and butyl isocyanate (41.5 grams, 0.419 moles) were added and the mixture was refluxed for one hour. The solvent was stripped off by using a rotary evaporator and the solution was filtered. The product was characterized by infrared bands at 3360, 2950, 1700, 1460, 1385, 1250, 1115, 1040, and 970 cm$^{-1}$.

EXAMPLE 16

2,5-Bis(2-acetoxybutylthio)-1,3,4-thiadiazole

The product was prepared substantially in accordance with Example 12 except that the epoxide was 1,2-epoxybutane. The product was characterized by the infrared bands at 2950, 1740, 1690, 1370, 1230, and 1095 cm$^{-1}$.

EXAMPLE 17

2,5-Bis[2-hydroxy-3-(2-ethylhexanoyloxy)propylthio]-1,3,4-thiadiazole

The product was prepared substantially by the method described in Example 9 except that the epoxide was glycidyl 2-ethylhexanoate. The product was characterized by the infrared absorption bands at 344Q, 2900, 1730, 1460, 1380, 1260, 1170, 1050, and 710 cm$^{-1}$.

EXAMPLE 18

2,5-Bis(2-hydroxy-3-oleoyloxypropylthio)-1,3,4-thiadiazole

The product was prepared substantially by the method described in Example 9 except that the epoxide was glycidyl oleate. The product was mixed with an equivalent amount of diluent mineral oil and filtered.

The product was characterized by the infrared absorption bands at 3440, 2900, 1740, 1460, 1380, 1250, 1170, 1110, 1050, 960, and 720 cm$^{-1}$.

EXAMPLE 19

2,5-Bis(2-acetoxy-3-oleoyloxypropylthio)-1,3,4-thiadiazole

The product of Example 18 was reacted with acetic anhydride according to the procedure described in Example 11. The product was characterized by the infrared absorption bands at 2900, 1750, 1460, 1370, 1230, 1160, 1050, 960, and 725 cm$^{-1}$.

EXAMPLE 20

The products of the invention were evaluated by the following tests.

1. Shell Four-Ball Wear Test

The test was conducted essentially according to the method described in ASTM D2266 procedure. Four highly polished steel balls 12.5 mm in diameter were placed in a test cup and submerged in the test sample. The test oil was Sunvis TM 21 manufactured by Sun Oil Company. The test was carried out at a rotation speed of 1800 rpm under a load of 20 kg at 54.5° C. and 40 kg at 93° C. for 60 minutes. The diameter of wear scar produced by samples containing additives of the invention was measured and the data compiled in Table I. The data indicate that the present additives have excellent antiwear properties even when present in quantities less than 0.01 percent.

TABLE I

Four-Ball Wear Test

| Sample | | Percent | Scar Diameter, mm 20 kg | 40 kg |
|---|---|---|---|---|
| 1 | None | — | 0.68 | 2.00 |
| 2 | 2,5-Bis(3-butoxy-2-acetoxypropylthio)-1,3,4-thiadiazole | 0.50 | 0.51 | 0.79 |
| 3 | 2,5-Bis(3-butoxy-2-acetoxypropylthio)-1,3,4-thiadiazole | 0.50 | — | 0.84 |
| 4 | 2,5-Bis(2-hydroxyhexadecylthio)-1,3,4-thiadiazole | 0.50 | 0.33 | 0.76 |
| 5 | 2,5-Bis(2-hydroxyhexadecylthio)-1,3,4-thiadiazole | 0.05 | — | 0.75 |
| 6 | 2,5-Bis(3-dodecyloxy-2-hydroxypropylthio)-1,3,4-thiadiazole | 0.50 | 0.49 | — |
| 7 | 2,5-Bis(3-dodecyloxy-2-hydroxypropylthio)-1,3,4-thiadiazole | 0.125 | — | 0.73 |
| 8 | 2,5-Bis(3-dodecyloxy-2-hydroxypropylthio)-1,3,4-thiadiazole | 0.0312 | — | 0.79 |
| 9 | 2,5-Bis(3-dodecyloxy-2-hydroxypropylsulfonyl)-1,3,4-thiadiazole | 0.50 | 0.57 | — |
| 10 | 2,5-Bis(3-dodecyloxy-2-hydroxypropylsulfonyl)-1,3,4-thiadiazole | 0.063 | — | 0.88 |
| 11 | 2,5-Bis(3-dodecyloxy-2-hydroxypropylsulfonyl)-1,3,4-thiadiazole | 0.0312 | — | 0.86 |
| 12 | 2,5-Bis(3-dodecyloxy-2-hydroxypropylsulfonyl)-1,3,4-thiadiazole | 0.0156 | — | 0.80 |
| 13 | 2,5-Bis(3-dodecyloxy-2-hydroxypropylsulfonyl)-1,3,4-thiadiazole | 0.0078 | — | 0.76 |

2. Timken Test

Lithium 12-hydroxystearate grease was formulated with 2,5-bis(3-dodecyloxy-2-hydroxypropylthio)-1,3,4-thiadiazole in the amounts given in Table II. The antiwear performance under extreme pressure conditions was evaluated by the Timken Test according to ASTM D-2907 procedure. The data compiled in Table II indicate excellent performance by the additive of the invention.

TABLE II

| | Timken Test Data | |
|---|---|---|
| Sample | Additive Percent | Timken Pass Load, kg |
| 14 | None | 20 |
| 15 | 2.0 | 30 |

TABLE II-continued

| | Timken Test Data | |
|---|---|---|
| Sample | Additive Percent | Timken Pass Load, kg |
| 16 | 3.0 | 55 |

3. Thin Film Oxygen Uptake Test

The test was conducted essentially according to the method described by Chia-Soon Ku et. al., J. Am. Soc. Lubricating Eng., 40,2 75-83, 1984. The oxidation induction time of the lubricant was measured under conditions which simulate the high temperature oxidation processes in automotive engines by a modified rotary bomb oxidation test method ASTM D-2272. The test was conducted with 1.5 gram samples of SAE-30 Oil formulated with catalyst obtained from the National Bureau of Standards. 2,5-Bis(3-dodecyloxy-2-hydroxypropylthio)-1,3,4-thiadiazole was added to the package in the amounts indicated in Table III. The test was conducted at 160° C. and initial oxygen pressure of 620.6 KPa (90 psi). A "pass" oil has a high induction time, while a "fail" oil has a low induction time. The additive of the invention has good antioxidant properties as shown by data compiled in Table III.

TABLE III

| | Thin Film Oxygen Uptake Test | |
|---|---|---|
| Sample | Additive Percent | Average Induction Time, Min. |
| 17 | None | 55 |
| 18 | 0.35 | 98 |
| 19 | 0.50 | 105 |

The above embodiments have shown various aspects of the present invention. Other variations will be evident to those skilled in the art and such modifications are intended to be within the scope of the invention as defined by the appended claims.

What is claimed is:

1. The compound 2,5-bis(3-dodecyloxy-2-hydroxypropylthio)-1,3,4-thiadiazole.

2. The compound 2,5-bis(2-hydroxyhexadecylthio)-1,3,4-thiadiazole.

3. The compound 2,5-bis(2-acetoxyhexadecylthio)-1,3,4-thiadiazole.

4. A composition comprising at least 40 percent by weight of water, from 0 to 15 percent by weight of a petroleum hydrocarbon oil or a synthetic oil and from about 0.1 to 10 percent by weight of 2,5-bis(2-hydroxymethyl-2-hydroxyethylthio)-1,3,4-thiadiazole.

* * * * *

UNITED STATES PATENT AND TRADEMARK OFFICE
CERTIFICATE OF CORRECTION

PATENT NO. : 5,026,865

DATED : June 25, 1991

INVENTOR(S) : Thomas J. Karol

It is certified that error appears in the above-identified patent and that said Letters Patent is hereby corrected as shown below:

Column 5, line 45
 "2,5-Bis(3-dodecyloxy-2-hydroxypropylthio-1,3,4-" should read
 -- 2,5-Bis(3-dodecyloxy-2-hydroxypropylthio)-1,3,4- --;

Column 5, line 60
 "2,5-Bis(3-octyloxy-2-hydroxypropylthio-1,3,4-" should read
 -- 2,5-Bis(3-octyloxy-2-hydroxypropylthio)-1,3,4- --;

Column 6, line 3
 "2,5-Bis(3-butyloxy-2-acetoxypropylthio-1,3,4-" should read
 -- 2,5-Bis(3-butyloxy-2-acetoxypropylthio)-1,3,4- --;

Column 6, line 19
 "2,5-Bis(2-hydroxyhexadecylthio)-1,3,4-thiadizole" should read
 -- 2,5-Bis(2-hydroxyhexadecylthio)-1,3,4-thiadiazole --;

Column 8, line 59
 "344Q" should read --3440--;

Column 9, Table I, Sample 3, Percent
 "0.50" should read -- 0.05 --.

Signed and Sealed this

Eighth Day of December, 1992

Attest:

DOUGLAS B. COMER

*Attesting Officer*         *Acting Commissioner of Patents and Trademarks*

UNITED STATES PATENT AND TRADEMARK OFFICE
CERTIFICATE OF CORRECTION

PATENT NO. : 5,026,865
DATED : June 25, 1991
INVENTOR(S) : Thomas J. Karol

It is certified that error appears in the above-identified patent and that said Letters Patent is hereby corrected as shown below:

Column 9, line 65 and column 10, line 4

"Timken Pass Load, kg" should read

--Timken Pass Load, lbs. --.

Signed and Sealed this

Twenty-ninth Day of March, 1994

Attest:

BRUCE LEHMAN

Attesting Officer     Commissioner of Patents and Trademarks